United States Patent [19]
Harada et al.

[11] Patent Number: 5,892,126
[45] Date of Patent: Apr. 6, 1999

[54] PROCESS FOR PREPARING 4-FLUORO-3-TRIFLUOROMETHYLPHENOL

[75] Inventors: Katsumasa Harada; Akio Matsushita; Yasuhiro Kawachi, all of Ube, Japan

[73] Assignee: Ube Industries, Ltd., Yamaguchi, Japan

[21] Appl. No.: 969,692

[22] Filed: Nov. 13, 1997

[30] Foreign Application Priority Data

Nov. 15, 1996 [JP] Japan .................................... 8-304925

[51] Int. Cl.$^6$ .................................................. C07C 39/24
[52] U.S. Cl. ............................................................ 568/775
[58] Field of Search ................................... 568/716, 774, 568/775, 778, 796

[56] References Cited

FOREIGN PATENT DOCUMENTS 01268658  10/1989  Japan .
03246244  11/1991  Japan .

Primary Examiner—Michael L. Shippen
Attorney, Agent, or Firm—David G. Conlin; Christine C. O'Day; Dike, Bronstein, Roberts & Cushman, LLP

[57] ABSTRACT

Disclosed is a process for preparing 4-fluoro-3-trifluoromethylphenol from 4-fluoro-3-trifluoromethylaniline, which comprises the steps of (1) using about 1 to 20 parts by weight of water based on 1 part by weight of 4-fluoro-3-trifluoromethylaniline in the presence of sulfuric acid to obtain 4-fluoro-3-trifluoromethylaniline sulfate; (2) subjecting the obtained 4-fluoro-3-trifluoromethylaniline sulfate to a diazotization reaction by using a diazotizing agent to obtain an aqueous solution containing about 8 to 25% by weight of a 4-fluoro-3-trifluoromethylbenzene-diazonium salt where a sulfuric acid concentration after diazotization is about 30 to 70% by weight in terms of the amount of sulfuric acid added, and the amount of water used is about 1 to 20 parts by weight based on 1 part by weight of 4-fluoro-3-trifluoromethylaniline; and (3) hydrolyzing the obtained 4-fluoro-3-trifluoromethylbenzenediazonium salt where a sulfuric acid concentration is about 30 to 70% by weight in terms of the amount of sulfuric acid added in a copper sulfate aqueous solution.

7 Claims, No Drawings

PROCESS FOR PREPARING 4-FLUORO-3-TRIFLUOROMETHYLPHENOL

BACKGROUND OF THE INVENTION

1. Field of the Invention

This invention relates to a process for preparing 4-fluoro-3-trifluoromethylphenol which is a starting material of an agricultural chemical.

2. Prior Art

"4-Fluoro-3-trifluoromethylphenol" (hereinafter also referred to as "the desired compound") is a compound which is useful as a starting material of an agricultural chemical.

For example, N-benzyl-2-(4-fluoro-3-trifluoromethylphenoxy)butanoic acid amide (a compound described in Japanese Provisional Patent Publication No. 10749/1988) which is used as a herbicide is synthesized through the desired compound.

As a process for preparing the desired compound from "4-fluoro-3-trifluoromethylaniline" (hereinafter also referred to as "the starting aniline"), there may be mentioned processes described in (1) Japanese Provisional Patent Publication No. 125245/1976, (2) Japanese Provisional Patent Publication No. 246244/1991, (3) J. Med. Chem., vol. 25, pp. 1097 to 1101 (1982) and (4) Japanese Provisional Patent Publication No. 268658/1989.

Further, as a process for preparing 4-fluorophenol from 4-fluoroaniline which is an analogue of the starting aniline, there may be mentioned a process described in (5) Japanese Provisional Patent Publication No. 316544/1994.

In the publication (5), it is described that a 4-fluorobenzenediazonium salt derived from 4-fluoroaniline has poor heat stability and a fluorine group at 4-position relative to a diazonium group which is an electron attractive group is easily substituted by a hydroxyl group (a defluorination-hydroxylation reaction). However, it is described that a defluorination-hydroxylation reaction does not occur at 15° to 25° C.

However, it could be confirmed that in the case of the starting aniline, a trifluoromethyl group at 3-position relative to a diazonium group further activates a reactivity of a fluorine group at 4-position by a hydroxyl group, whereby a defluorination-hydroxylation reaction at 4-position occurs even at room temperature.

That is, the present inventors have isolated 2-trifluoromethyl-4-diazocyclohexa-2,5-dienone with a yield of 88% showing that a defluorination-hydroxylation reaction proceeds by preparing "a 4-fluoro-3-trifluoromethylbenzenediazonium salt" (hereinafter also referred to as "the diazonium salt"), retaining the diazonium salt at room temperature for 24 hours and then neutralizing it with sodium carbonate according to a method as shown in Reference example 1 described below.

It is considered that the reason why the diazonium salt is extremely unstable in this case is not merely that its stability to temperature is poor but that such a problem is caused by neutralization operation using sodium carbonate.

Even in the case of a method in which the diazonium salt is retained at 0° to 5° C. at which better temperature stability is given as compared with retention at room temperature as shown in Comparative example 5 described below, an amount of the desired compound is reduced by 42% after 24 hours.

From these two facts, it can be seen that a main side reaction is a defluorination-hydroxylation reaction of the diazonium salt due to heat.

Also, from a result of preparing the diazonium salt by the process described in the publication (4) and examining the stability of the diazonium salt at 0° C., it has been found that the same by-product as described above is produced with the lapse of time (it was produced by about 15% in 24 hours) to lower the yield of the desired compound.

Therefore, it has been clarified that when the diazonium salt is prepared from the starting aniline under preparation conditions of 4-fluoro-3-trifluoromethylphenol described in the publication (4), there is a problem that the yield of the diazonium salt is lowered by a side reaction in which fluorine at 4-position is subjected to a defluorination-hydroxylation reaction, whereby lowering of the yield of the desired compound is brought about.

From the foregoing, it has been found that in order to heighten the yield of the desired compound, it is extremely important to heighten the stability of the diazonium salt.

Incidentally, in the above publications and literature (1) to (4), the desired compound can be obtained through the respective steps of preparing "sulfate of the starting aniline" (hereinafter also referred to as "the starting aniline sulfate"), diazotizing the starting aniline sulfate and hydrolyzing the resulting diazonium salt. It has been considered that the diazotization reaction step is an exothermic reaction accompanied with high heat and the produced diazonium salt has poor heat stability so that a method of effecting a diazotization reaction at 0° to 10° C. has been used.

However, a time required for preparing the desired compound on an industrial level is much longer than a time required on an experimental level as in the above publications and literature (1) to (4).

This fact means that lowering of the yield of the desired compound is brought about in industrial production.

Incidentally, one of the important factors for reducing fixed cost in industrial production of the desired compound is to heighten a substrate concentration in order to heighten productivity.

Although the diazonium salt concentrations described in the publications (1) and (2) are high, an isolation yield is as low as 52% in the publication (1), and it is described in the publication (2) that the desired compound was obtained with a yield of 85%, but the desired compound could be obtained only with a reaction yield of 25% in a tracing experiment by the present inventors.

In tracing experiments of the literature (3) and the publication (4) by the present inventors, it could be confirmed that the desired compound could be obtained with a high yield and a yield at 0° C. after 24 hours of the literature (3) is not decreased, but productivity was poor due to a low diazonium salt concentration.

The desired compound is obtained through the steps of preparing sulfate of the starting aniline, diazotizing the sulfate and hydrolyzing the resulting diazonium salt.

Therefore, in the case where a substrate concentration is heightened, in the step of preparing the starting aniline (an exothermic reaction), such a fear that the starting aniline sulfate is precipitated (scaling) in a reaction tank during cooling to the temperature (0° to 5° C.) of a diazotization reaction, and a thermal conductivity coefficient is lowered to worsen a cooling effect is increased. Further, the diazotization reaction is an exothermic reaction so that a diazotizing agent is reacted under cooling. When excessive cooling is effected, a part of the starting aniline sulfate which has been dissolved is reprecipitated, and further, inorganic substances such as sodium sulfate are precipitated, whereby a cooling efficiency is worsened.

As temperature is controlled strictly so that excessive cooling is not effected in order to avoid such a fear, a time required for adding a diazotizing agent is elongated.

Thus, when a substrate concentration is heightened, long and strict temperature control is required, and various troubles are liable to be caused.

Due to the troubles, the yield of the desired compound is lowered.

As described above, in the above publications and literature (1) to (4), processes for preparing the desired compound are described, but it is not disclosed that the yield of the desired compound greatly depends on the stability of the diazonium salt in a process for preparing the desired compound on an industrial scale.

That is, in the above publications and literature (1) to (4), it is not disclosed that the stability of the diazonium salt is intended to be heightened and the desired compound can be obtained with a high yield by using the diazonium salt retained at a high concentration.

SUMMARY OF THE INVENTION

An object of the present invention is to provide a novel process for preparing the desired compound (4-fluoro-3-trifluoromethylphenol) which is important as a synthetic starting material for preparing N-benzyl-2-(4-fluoro-3-trifluoromethylphenoxy)butanoic acid amide which is used as a herbicide, easily and industrially with a good yield.

The present inventors have studied in order to achieve the above object and consequently found a novel process for preparing the desired compound easily and industrially with a good yield to accomplish the present invention.

That is, the present invention relates to a process for preparing 4-fluoro-3-trifluoromethylphenol from 4-fluoro-3-trifluoromethylaniline, which comprises the steps of:

(1) using about 1 to 20 parts by weight of water based on 1 part by weight of 4-fluoro-3-trifluoromethylaniline in the presence of sulfuric acid to obtain 4-fluoro-3-trifluoromethylaniline sulfate;

(2) subjecting the obtained 4-fluoro-3-trifluoromethylaniline sulfate to a diazotization reaction by using a diazotizing agent to obtain an aqueous solution containing about 8 to 25% by weight of a 4-fluoro-3-trifluoromethylbenzenediazonium salt where a sulfuric acid concentration after diazotization is about 30 to 70% by weight in terms of the amount of sulfuric acid added, and the amount of water used is about 1 to 20 parts by weight based on 1 part by weight of 4-fluoro-3-trifluoromethylaniline; and (3) hydrolyzing the obtained 4-fluoro-3-trifluoromethylbenzenediazonium salt where a sulfuric acid concentration is about 30 to 70% by weight in terms of the amount of sulfuric acid added, in a copper sulfate aqueous solution.

DESCRIPTION OF THE PREFERRED EMBODIMENTS

In the following, the present invention is explained in detail.

The process for preparing the desired compound of the present invention comprises (1) a step of preparing the starting aniline sulfate, (2) a step of preparing the diazonium salt by a diazotization reaction of the starting aniline sulfate and (3) a step of hydrolyzing the produced diazonium salt as shown below.

(1) Step of Preparing the Starting Aniline Sulfate

In this step, the starting aniline sulfate is obtained by using the starting aniline as a starting material in the presence of sulfuric acid.

A sulfuric acid concentration is not particularly limited so long as an object of obtaining the starting aniline sulfate can be achieved, and it is preferably 35 to 70%.

As a method for preparing the starting aniline sulfate, there may be mentioned a method of mixing the starting aniline, sulfuric acid and water and dissolving them under heating, and a method of adding the starting aniline to a mixture of sulfuric acid and water.

The above dissolution under heating can be performed at 50° to 100° C., preferably 70° to 90° C.

The ratio of the starting aniline to water to be used in the presence of sulfuric acid is about 1 to 20 parts by weight, preferably about 2 to 11 parts by weight of water based on 1 part by weight of the starting aniline.

The amount of water used based on 1 part by weight of the starting aniline in this step is a total amount of various weights of water contained in sulfuric acid and water used.

As the water used, there may be mentioned water used for diluting a starting material such as concentrated sulfuric acid.

The ratio of the starting aniline and sulfuric acid to be used is about 2 to 7.5 parts by weight of sulfuric acid (sulfuric acid concentration: about 30 to 70% by weight) based on 1 part by weight of the starting aniline.

That is, if the sulfuric acid concentration is less than 30% by weight, the stability of the diazonium salt obtained after the next diazotization reaction step is worsened to lower yield so that in order to maintain its stability, operation of further adding sulfuric acid becomes necessary in the diazotization reaction step. If it exceeds 70%, the diazotization reaction does not proceed smoothly to lower yield.

The sulfuric acid concentration described in the present specification is a concentration value represented by the following numerical formula.

$$\text{Sulfuric acid concentration} = \frac{A}{B} \times 100(\%)$$

A and B in the above numerical formula have the following meanings.

A: Weight after purity calculation of sulfuric acid used (weight of pure sulfuric acid)

B: Respective weights of the starting aniline, concentrated sulfuric acid and water used With respect to B, in "(2) Diazotization reaction step" described in the next item, the respective weights of a diazotizing agent and water for dissolving the diazotizing agent are further added.

(2) Diazotization Reaction Step

In this step, an aqueous solution of about 8 to 25% by weight of the diazonium salt, i.e., a 4-fluoro-3-trifluoromethylbenzenediazonium salt, can be obtained by diazotizing the starting aniline sulfate obtained in the above (1) by a diazotizing agent.

The concentration of the diazonium salt in this step is a concentration value represented by the following numerical formula (the diazotization reaction is considered to proceed 100%, and the concentration of the diazonium salt is calculated in terms of hydrogen sulfate).

$$\text{Concentration of diazonium salt} = \frac{C \times 288}{D} \times 100(\%)$$

C and D in the above numerical formula have the following meanings.
C: Molar number of the starting aniline
D: Respective weights of the starting aniline, concentrated sulfuric acid, water used and a diazotizing agent As water used in D, there may be mentioned water used for diluting or dissolving a starting material (dilution of concentrated sulfuric acid, dissolution of a diazotizing agent or the like).

The resulting diazonium salt aqueous solution is preferably retained at the diazotization reaction temperature and used in the next hydrolysis step.

Also, an excessive amount of the diazotizing agent in the resulting diazonium salt aqueous solution can be removed by decomposing it with urea.

As the diazotizing agent, there may be mentioned nitrosyl sulfate and a nitrite such as alkyl nitrite, sodium nitrite and potassium nitrite, preferably a nitrite, more preferably sodium nitrite.

The amount of the diazotizing agent to be used is about 1 to 2 mole, preferably about 1 to 1.3 mole based on 1 mole of the starting aniline.

The diazotizing agent may be added as an aqueous solution obtained by dissolving it with a small amount of water.

The reaction temperature of the diazotization reaction is about 30° C. or lower, preferably about 0° to 10° C.

The reaction time of the diazotization reaction is about 0.5 to 3 hours, but may be changed suitably depending on a reaction scale.

The resulting diazonium salt can be maintained at a high concentration of about 8 to 25% by weight even when it is retained at about 0° to 5° C. for 24 hours since the stability of the diazonium salt obtained in this reaction step and the stability of the diazonium salt in the next hydrolysis step are kept. The content of a by-product in the diazonium salt aqueous solution is about 0.7% by weight or less, and the ratio of the by-product in the diazonium salt aqueous solution is about 5 mole % by weight or less.

As the by-product, there may be mentioned 2-trifluoromethyl-4-diazocyclohexa-2,5-dienone and a diazo coupling compound, and a main component thereof is 2-trifluoromethyl-4-diazocyclohexa-2,5-dienone.

The yield of the desired compound is higher as the stability of the diazonium salt is higher.

In order to keep the stability of the diazonium salt, it is necessary that the sulfuric acid concentration of this diazonium salt aqueous solution is a high concentration of about 30 to 70% by weight in terms of the total amount of sulfuric acid added. The sulfuric acid concentration is preferably about 31 to 65% by weight, more preferably about 33 to 63% by weight.

When the sulfuric acid concentration of the diazonium salt aqueous solution is within the range of a concentration at which the stability of the diazonium salt can be kept, the object of the present invention can be achieved even when the amount of a starting material to be added and the time of addition thereof are changed as desired.

If the amount of water to be used is large and the sulfuric acid concentration falls outside the above range, the stability of the diazonium salt is worsened while if said amount is small, it is difficult to perform stirring operation, and the diazotization reaction does not proceed with good reproduction. Therefore, the amount of water to be used is about 1 to 20 parts by weight, preferably about 1.5 to 11 parts by weight, more preferably about 2 to 4.5 parts by weight based on 1 part by weight of the starting aniline so that the sulfuric acid concentration falls within the above range.

The amount of water used based on 1 part by weight of the starting aniline in this step is a total amount of the respective weights of water contained in sulfuric acid, water used and water produced in the diazotization reaction (when water is used for dissolving the diazotizing agent, its weight is also added).

The weight of water produced in the diazotization reaction is an amount of water produced when the diazotization reaction is considered to proceed 100% (for example, when sodium nitrite is used as the diazotizing agent, two equivalents of water is produced).

(3) Hydrolysis Step

The sulfuric acid concentration at that time of the above diazonium salt is maintained, and at suitable reaction temperature, the diazonium salt is hydrolyzed by adding the diazonium salt aqueous solution to a copper sulfate aqueous solution to obtain the desired compound.

The concentration of the diazonium salt to be used is about 8 to 25% by weight, preferably about 14 to 22% by weight.

The copper sulfate aqueous solution can be prepared by adding about 0.3 to 1.5 mole of copper sulfate based on 1 mole of the starting aniline to water; and the amount of water to be used is preferably about 0.5 to 5 parts by weight based on 1 part by weight of copper sulfate pentahydrate, which is an amount by which a solution state of the copper sulfate aqueous solution can be retained under a hydrolysis temperature condition.

The desired compound can be hydrolyzed, separated and obtained by a conventional method such as a steam distillation method and a solvent extraction method.

The reaction temperature of hydrolysis is about 100° to 150° C., preferably about 110° to 140° C. in the case of using a steam distillation method, but it is about 75° to 95° C. in the case of using a solvent extraction method. Yield is lowered when the temperature falls outside this range.

In the steam distillation method, the diazonium salt aqueous solution is added dropwise to the copper sulfate aqueous solution to obtain the desired compound, and the a desired compound is distilled out together with steam to the outside of the reaction system.

In this case, since the desired compound is in a state of a mixture with water, isolation and purification thereof can be performed by a method of saturating the mixture with sodium chloride and then separating the desired compound, a method of extracting the desired compound by using an organic solvent such as toluene, ethyl acetate, dichloroethane and the like, or a method in which the above methods are combined.

In the solvent extraction method, the diazonium salt aqueous solution is added dropwise to a mixed solvent of the copper sulfate aqueous solution and a water-insoluble solvent such as a solvent comprising at least one of toluene, xylene and chlorobenzene to obtain the desired compound, and the desired compound is separated from the copper sulfate aqueous solution.

In this case, separation and extraction may be performed after completion of the reaction, and isolation and purification of the desired compound themselves are not particularly required, but distillation can be performed after concentration.

If the amount of the water-insoluble solvent to be used in the solvent extraction method is less than 1 part by weight, side reaction products such as a coupling product are increased to lower yield while if said amount exceeds 10 parts by weight, a large amount of the solvent is used, which is not preferred in the point of economy. Therefore, the amount of the water-insoluble solvent to be used is about 1 to 10 parts by weight, preferably about 1.2 to 7 parts by weight based on 1 part by weight of the starting aniline.

EXAMPLES

The present invention is described in detail by referring to Examples, Comparative examples and Reference example.

Example 1-1

At room temperature, 29.5 g (289 mmol) of concentrated sulfuric acid, 32 g of water and 10 g (56 mmol) of 4-fluoro-3-trifluoromethylaniline were mixed, and the mixture was stirred under heating up to about 80° C. to prepare a uniform solution. Thereafter, the uniform solution was cooled to 10° C. or lower.

Then, a solution obtained by dissolving 5 g (72 mmol) of sodium nitrite in 6 g of water was added dropwise to the above mixture under stirring.

At the time of this dropwise addition, the temperature of the solution was retained at 10° C or lower. After dropwise addition, the mixture was retained at 5° C. for 30 minutes, and then 2 g (33 mmol) of urea was added thereto.

The diazonium salt aqueous solution prepared as described above was retained at 5° C.

Then, a mixed solvent of 13 g (52 mmol) of copper sulfate pentahydrate, 32 g of water and 39 g of toluene was heated to 85° C. Under stirring while retaining this temperature, the above diazonium salt aqueous solution was added dropwise to the mixed solvent over 30 minutes.

After completion of dropwise addition, the mixture was cooled, the toluene layer was separated, and the residual aqueous layer was extracted once with 17.3 g of toluene.

The toluene layer was combined with the extract, and a product was quantitated by gas chromatography according to the internal standard method to find that the yield of 4-fluoro-3-trifluoromethylphenol was 86%

Next, "the amount of water used based on 1 part by weight of the starting aniline after diazotization at a sulfuric acid concentration of 30 to 70% by weight in terms of the amount of sulfuric acid added" (hereinafter referred to as "amount of water"), "the concentration of the diazonium salt in the diazonium salt aqueous solution obtained by diazotization (the sulfuric acid concentration after diazotization is 30 to 70% by weight in terms of the amount of sulfuric acid added)" (hereinafter referred to as "diazonium salt concentration") and the sulfuric acid concentration are shown.

Amount of water: 4.12 parts by weight

Diazonium salt concentration: 19.5%

Sulfuric acid concentration after diazotization: 34.3% by weight.

Example 1-2

Procedures were performed in the same manner as in Example 1-1 except for retaining the diazonium salt at 0° to 5° C. for 24 hours, and a product was quantitated by gas chromatography according to the internal standard method to find that the yield of 4-fluoro-3-trifluoromethylphenol was 85%.

From the difference between this yield and the yield of Example 1-1, "the content of the by-product (mole %) in the diazonium aqueous solution retained at 0° to 5° C. for 24 hours" (hereinafter referred to as "content of by-product") is as shown below. Also, "the content of the by-product in the diazonium salt aqueous solution determined by calculation based on the content of the by-product" (hereinafter referred to as "content in solution") is also shown.

Content of by-product: 1 mole % (content in solution: 0.7% by weight or less).

Example 2-1

Procedures were performed in the same manner as in Example 1-1 except for using 44.2 g (433 mmol) of concentrated sulfuric acid, and a product was quantitated by gas chromatography according to the internal standard method to find that the yield of 4-fluoro-3-trifluoromethylphenol was 88%.

Amount of water: 4.18 parts by weight

Diazonium salt concentration: 16.6%

Sulfuric acid concentration after diazotization: 43.7% by weight.

Example 2-2

Procedures were performed in the same manner as in Example 1-2 except for using 44.2 g (433 mmol) of concentrated sulfuric acid, and a product was quantitated by gas chromatography according to the internal standard method to find that the yield of 4-fluoro-3-trifluoromethylphenol was 87%.

Content of by-product: 1 mole % (content in solution: 0.7% by weight or less).

Example 3-1

Procedures were performed in the same manner as in Example 1-1 except for using 58.9 g (577 mmol) of concentrated sulfuric acid, and a product was quantitated by gas chromatography according to the internal standard method to find that the yield of 4-fluoro-3-trifluoromethylphenol was 86%.

Amount of water: 4.24 parts by weight

Diazonium salt concentration: 14.4%

Sulfuric acid concentration after diazotization: 50.5% by weight.

Example 3-2

Procedures were performed in the same manner as in Example 1-2 except for using 58.9 g (577 mmol) of concentrated sulfuric acid, and a product was quantitated by gas chromatography according to the internal standard method to find that the yield of 4-fluoro-3-trifluoromethylphenol was 87%.

Content of by-product: 1 mole % or less (content in solution: 0.7 by weight % or less).

Example 4

At room temperature, 29.5 g (289 mmol) of concentrated sulfuric acid, 32 g of water and 10 g (56 mmol) of 4-fluoro-3-trifluoromethylaniline were mixed, and the mixture was cooled to 10° C. or lower.

Subsequent procedures were performed in the same manner as in Example 1-1, and a product was quantitated by gas chromatography according to the internal standard method to find that the yield of 4-fluoro-3-trifluoromethylphenol was 87%.

Amount of water: 4.12 parts by weight

Diazonium salt concentration: 19.5%

Sulfuric acid concentration after diazotization: 34.3% by weight

Example 5

Procedures were performed in the same manner as in Example 1-1 except for performing diazotization at 12° C., and a product was quantitated by gas chromatography according to the internal standard method to find that the yield of 4-fluoro-3-trifluoromethylphenol was 88%.

Amount of water: 4.12 parts by weight

Diazonium salt concentration: 19.5%

Sulfuric acid concentration after diazotization: 34.3% by weight.

Example 6

Procedures were performed in the same manner as in Example 2-1 except for performing diazotization at room temperature (22° C.), and a product was quantitated by gas chromatography according to the internal standard method to find that the yield of 4-fluoro-3-trifluoromethylphenol was 86%.

Amount of water: 4.18 parts by weight

Diazonium salt concentration: 16.6%

Sulfuric acid concentration after diazotization: 43.7% by weight.

Example 7

Procedures were performed in the same manner as in Example 3-1 except for performing diazotization at room temperature (22° C.), and a product was quantitated by gas chromatography according to the internal standard method to find that the yield of 4-fluoro-3-trifluoromethylphenol was 85%.

Amount of water: 4.24 parts by weight

Diazonium salt concentration: 14.4%

Sulfuric acid concentration after diazotization: 50.5% by weight.

Example 8

Procedures were performed in the same manner as in Example except for using 10 g of water and 17.3 g of toluene in the hydrolysis reaction, and a product was quantitated by gas chromatography according to the internal standard method to find that the yield of 4-fluoro-3-trifluoromethylphenol was 87%.

Amount of water: 4.12 parts by weight

Diazonium salt concentration: 19.5%

Sulfuric acid concentration after diazotization: 34.3% by weight.

Example 9-1

At room temperature, 63.5 g (622 mmol) of concentrated sulfuric acid, 69 g of water and 10 g (56 mmol) of 4-fluoro-3-trifluoromethylaniline were mixed, and the mixture was stirred under heating to about 80° C. to prepare a uniform solution. Thereafter, the uniform solution was cooled to 10° C. or lower.

Then, a solution obtained by dissolving 4.5 g (59 mmol) of sodium nitrite in 6.9 g of water was added dropwise to the above reaction mixture under stirring.

At the time of this dropwise addition, the temperature of the solution was retained at 10° C. or lower. After dropwise addition, the mixture was retained at 5° C. for 30 minutes, and then 0.5 g (8.3 mmol) of urea was added thereto.

The diazonium salt aqueous solution prepared as described above was retained at 5° C.

Then, a mixed solvent of 13 g (52 mmol) of copper sulfate pentahydrate, 32 g of water and 39 g of toluene was heated to 85° C. Under stirring while retaining this temperature, the above diazonium salt aqueous solution was added dropwise to the mixed solvent over 30 minutes.

After completion of dropwise addition, the mixture was cooled, the toluene layer was separated, and the residual aqueous layer was extracted once with 17.3 g of toluene.

The toluene layer was combined with the extract, and a product was quantitated by gas chromatography according to the internal standard method to find that the yield of 4-fluoro-3-trifluoromethylphenol was 90%.

Amount of water: 8.05 parts by weight

Diazonium salt concentration: 10.5%

Sulfuric acid concentration after diazotization: 39.6% by weight.

Example 9-2

Procedures were performed in the same manner as in Example 9-1 except for retaining the diazonium salt at 0° to 5° C. for 24 hours, and a product was quantitated by gas chromatography according to the internal standard method to find that the yield of 4-fluoro-3-trifluoromethylphenol was 86%.

Content of by-product: 4 mole % (content in solution: 0.7% by weight or less).

Example 10-1

At room temperature, 45.7 g (448 mmol) of concentrated sulfuric acid, 65 g of water and 10 g (56 mmol) of 4-fluoro-3-trifluoromethylaniline were mixed, and the mixture was cooled to 10° C. or lower.

Then, a solution obtained by dissolving 4.2 g (61 mmol) of sodium nitrite in 6.5 g of water was added dropwise to the above reaction mixture under stirring.

At the time of this dropwise addition, the temperature of the solution was retained at 10° C. or lower. After dropwise addition, the mixture was retained at 5° C. for 30 minutes, and then 0.33 g (5.4 mmol) of urea was added thereto.

The diazonium salt aqueous solution prepared as described above was retained at 5° C.

Then, a mixed solvent of 13 g (52 mmol) of copper sulfate pentahydrate, 32 g of water and 39 g of toluene was heated to 85° C. Under stirring while retaining this temperature, the above diazonium salt aqueous solution was added dropwise to the mixed solvent over 30 minutes.

After completion of dropwise addition, the mixture was cooled, the toluene layer was separated, and the residual aqueous layer was extracted once with 17.3 g of toluene.

The toluene layer was combined with the extract, and a product was quantitated by gas chromatography according to the internal standard method to find that the yield of 4-fluoro-3-trifluoromethylphenol was 87%.

Amount of water: 7.53 parts by weight

Diazonium salt concentration: 12.3%

Sulfuric acid concentration after diazotization: 33.4% by weight.

Example 10-2

Procedures were performed in the same manner as in Example 10-1 except for retaining the diazonium salt at 0° to 5° C. for 24 hours, and a product was quantitated by gas chromatography according to the internal standard method to find that the yield of 4-fluoro-3-trifluoromethylphenol was 85%.

Content of by-product: 2 mole % (content in solution: 0.7% by weight or less).

Example 11

At room temperature, 147.2 g (1.44 mol) of concentrated sulfuric acid, 160 g of water and 50 g (279 mmol) of 4-fluoro-3-trifluoromethylaniline were mixed, and the mixture was cooled to 10° C. or lower.

Then, a solution obtained by dissolving 22 g (318 mmol) of sodium nitrite in 30 g of water was added dropwise to the above reaction mixture under stirring.

At the time of this dropwise addition, the temperature of the solution was retained at 10° C. or lower. After dropwise addition, the mixture was retained at 5° C. for 30 minutes, and then 8.3 g (138 mmol) of urea was added thereto.

The diazonium salt aqueous solution prepared as described above was retained at 5° C.

Then, a mixture of 65 g (260 mmol) of copper sulfate pentahydrate and 50 g of water was refluxed under heating.

While introducing steam into the mixture, the above diazonium salt aqueous solution was added dropwise to the mixture over 2 hours and 20 minutes.

The internal temperature of a hydrolysis tank was 98° to 110° C.

After dropwise addition of the diazonium salt aqueous solution, steam distillation was effected for 45 minutes.

The total effluent amount was about 750 ml. The effluent was extracted twice with 200 ml of toluene and once with 50 ml of toluene.

A product was quantitated by gas chromatography according to the internal standard method to find that the yield of 4-fluoro-3-trifluoromethylphenol was 96%.

Amount of water: 4.12 parts by weight

Diazonium salt concentration: 19.5%

Sulfuric acid concentration after diazotization: 34.3% by weight.

Comparative Example 1

At room temperature, 30.9 g (303 mmol) of concentrated sulfuric acid, 65 g of water and 10 g (56 mmol) of 4-fluoro-3-trifluoromethylaniline were mixed, and the mixture was stirred under heating to about 80° C. to prepare a uniform solution. Thereafter, the uniform solution was cooled to 10° C. or lower.

Then, a solution obtained by dissolving 4.2 g (61 mmol) of sodium nitrite in 6.5 g of water was added dropwise to the above reaction mixture under stirring.

At the time of this dropwise addition, the temperature of the solution was retained at 10° C. or lower. After dropwise addition, the mixture was retained at 5° C. for 30 minutes, and then 0.33 g (5.4 mmol) of urea was added thereto.

The diazonium salt aqueous solution prepared as described above was retained at 0° to 5° C. for 24 hours.

Then, a mixed solvent of 14 g (56 mmol) of copper sulfate pentahydrate, 32.5 g of water and 47 g of toluene was heated to 85° C. Under stirring while retaining this temperature, the above diazonium salt aqueous solution was added dropwise to the mixed solvent over 30 minutes.

After completion of dropwise addition, the mixture was cooled, the toluene layer was separated, and the residual aqueous layer was extracted once with 17.3 g of toluene.

The toluene layer was combined with the extract, and a product was quantitated by gas chromatography according to the internal standard method to find that the yield of 4-fluoro-3-trifluoromethylphenol was 74%.

Amount of water: 7.48 parts by weight

Diazonium salt concentration: 13.8%

Sulfuric acid concentration after diazotization: 25.4% by weight

Content of by-product: 15 mole % (content in solution: 1.4% by weight).

Comparative Example 2

Procedures were performed in the same manner as in Example 1-2 except for using 14.7 g (144 mmol) of concentrated sulfuric acid and adding no urea after diazotization, and a product was quantitated by gas chromatography according to the internal standard method to find that the yield of 4-fluoro-3-trifluoromethylphenol was 56%.

Amount of water: 4.06 parts by weight

Diazonium salt concentration: 23.8%

Sulfuric acid concentration after diazotization: 20.8% by weight

Content of by-product: 29 mole % (content in solution: 4.5 % by weight).

Comparative Example 3

At room temperature, 16.4 g (161 mmol) of concentrated sulfuric acid, 16 g of water and 10 g (56 mmol) of 4-fluoro-3-trifluoromethylaniline were mixed, and the mixture was cooled to 10° C. or lower.

Then, a solution obtained by dissolving 4.4 g (64 mmol) of sodium nitrite in 6 g of water was added dropwise to the above reaction mixture under stirring.

At the time of this dropwise addition, the temperature of the solution was retained at 10° C. or lower. After dropwise addition, the mixture was retained at 5° C. for 30 minutes, and then 1.67 g (27.8 mmol) of urea was added thereto.

The diazonium salt aqueous solution prepared as described above was retained at 0° to 5° C. for 24 hours.

Then, a mixed solvent of 13 g (56 mmol) of copper sulfate pentahydrate, 10 g of water and 17.3 g of toluene was heated to 85° C. Under stirring while retaining this temperature, the above diazonium salt aqueous solution was added dropwise to the mixed solvent over 30 minutes.

After completion of dropwise addition, the mixture was cooled, the toluene layer was separated, and the residual aqueous layer was extracted once with 17.3 g of toluene.

The toluene layer was combined with the extract, and a product was quantitated by gas chromatography according to the internal standard method to find that the yield of 4-fluoro-3-trifluoromethylphenol was 56%.

Amount of water: 2.47 parts by weight

Diazonium salt concentration: 30.5%

Sulfuric acid concentration after diazotization: 29.8% by weight

Content of by-product: 24 mole % (content in solution: 4.8 % by weight).

Comparative Example 4

At room temperature, 29.4 g (288 mmol) of concentrated sulfuric acid, 48 g of water and 10 g (56 mmol) of 4-fluoro-3-trifluoromethylaniline were mixed, and the mixture was stirred under heating to about 80° C. to prepare a uniform solution. Thereafter, the uniform solution was cooled to 10° C. or lower.

Then, a solution obtained by dissolving 4 g (58 mmol) of sodium nitrite in 6 g of water was added dropwise to the above reaction mixture under stirring.

At the time of this dropwise addition, the temperature of the solution was retained at 10° C. or lower. After dropwise addition, the mixture was retained at 5° C. for 30 minutes.

The diazonium salt aqueous solution prepared as described above was retained at 0° to 5° C. for 24 hours.

Then, a mixed solvent of 13 g (52 mmol) of copper sulfate pentahydrate, 10 g of water and 17.3 g of toluene was heated to 85° C. Under stirring while retaining this temperature, the above diazonium salt aqueous solution was added dropwise to the mixed solvent over 30 minutes.

After completion of dropwise addition, the mixture was cooled, the toluene layer was separated, and the residual aqueous layer was extracted once with 17.3 g of toluene.

The toluene layer was combined with the extract, and a product was quantitated by gas chromatography according to the internal standard method to find that the yield of 4-fluoro-3-trifluoromethylphenol was 76%.

Amount of water: 5.72 parts by weight

Diazonium salt concentration: 16.6%

Sulfuric acid concentration after diazotization: 29.0% by weight

Content of by-product: 15 mole % (content in solution: 1.6% by weight).

Comparative Example 5

At room temperature, 6.3 g (62 mmol) of concentrated sulfuric acid, 56 g of water and 10 g (56 mmol) of 4-fluoro-3-trifluoromethylaniline were mixed, and the mixture was cooled to 10° C. or lower.

Then, a solution obtained by dissolving 4.0 g (58 mmol) of sodium nitrite in 28 g of water was added dropwise to the above reaction mixture under stirring.

At the time of this dropwise addition, the temperature of the solution was retained at 10° C. or lower. After dropwise addition, the mixture was retained at 5° C. for 30 minutes.

The diazonium salt aqueous solution prepared as described above was retained at 0° to 5° C. for 24 hours.

Then, a mixed solvent of 13 g (52 mmol) of copper sulfate pentahydrate, 32 g of water and 39 g of toluene was heated to 85° C. Under stirring while retaining this temperature, the above diazonium salt aqueous solution was added dropwise to the mixed solvent over 30 minutes.

After completion of dropwise addition, the mixture was cooled, the toluene layer was separated, and the residual aqueous layer was extracted once with 17.3 g of toluene.

The toluene layer was combined with the extract, and a product was quantitated by gas chromatography according to the internal standard method to find that the yield of 4-fluoro-3-trifluoromethylphenol was 15%.

Amount of water: 8.63 parts by weight

Diazonium salt concentration: 15.5%

Sulfuric acid concentration after diazotization: 5.8% by weight

Content of by-product: 42 mole % (content in solution: 4.2% by weight).

Reference Example 1

A diazonium salt aqueous solution prepared in the same manner as in Comparative example 5 was left to stand at 25° C. for 24 hours.

A saturated sodium carbonate aqueous solution was added to the diazonium salt aqueous solution to make the solution alkaline (pH=7.5).

The solution was extracted once with 100 ml of dichloroethane and three times with 50 ml of dichloroethane.

After concentrating the combined extracts, the condensate was subjected to column chromatography treatment (silica gel-ethyl acetate) to obtain 9.19 g (yield: 88%) of 2-trifluoromethyl-4-diazocyclohexa-2,5-dienone (a defluorinated-hydroxylated derivative of a 4-fluoro-3-trifluoromethylbenzenediazonium salt).

In consideration of the above result and the result of Comparative example 5 described above, the above result shows that a defluorination-hydroxylation reaction of a 4-fluoro-3-trifluoromethylbenzendiazonium salt is caused by heat to convert said salt into a 4-hydroxy-3-trifluoromethylbenzenediazonium salt, a stable diazonium salt is formed in this state, or deprotonation is further caused and said salt exists stably as a sulfate of 2-trifluoromethyl-4-diazocyclohexa-2,5-dienone.

The physical properties of 2-trifluoromethyl-4-diazocyclohexa-2,5-dienone are shown below.

$^1$H-NMR (400 MHz, CDCl$_3$) δ (ppm): 6.51 (d, 1H, J=9.77 Hz), 7.43 (dd, 1H, J=9.77 Hz, 2.93 Hz), 7.89 (dd, 1H, J=2.93 Hz, 0.98 Hz).

CIMS (m/e): 189 (M+1).

Elemental analysis value (in terms of C$_7$H$_3$F$_3$N$_2$O).

| Element | C | H | N |
| --- | --- | --- | --- |
| Theoretical value (%) | 44.70 | 1.61 | 14.89 |
| Measured value (%) | 44.69 | 1.63 | 14.80 |

According to the present invention, 4-fluoro-3-trifluoromethylphenol which is important as a synthetic starting material of N-benzyl-2-(4-fluoro-3-trifluoromethylphenoxy)-butanoic acid amide used as a herbicide can be prepared easily and industrially with a good yield.

We claim:

1. A process for preparing 4-fluoro-3-trifluoromethylphenol from 4-fluoro-3-trifluoromethylaniline, which comprises the steps of:

(1) using about 1 to 20 parts by weight of water based on 1 part by weight of 4-fluoro-3-trifluoromethylaniline in the presence of sulfuric acid to obtain 4-fluoro-3-trifluoromethylaniline sulfate;

(2) subjecting the obtained 4-fluoro-3-trifluoromethylaniine sulfate to a diazotization reaction by using a diazotizing agent to obtain an aqueous solution containing about 8–25% by weight of a 4-fluoro-3-trifluoromethylbenzenediazonium salt where a sulfuric acid concentration after diazotization is about 30–70% by weight in terms of the amount of sulfuric acid added during the diazotization reaction, and the amount of water used is about 1 to 20 parts by weight based on 1 part by weight of 4-fluoro-3-trifluoromethylaniline; and (3) hydrolyzing the obtained 4-fluoro-3-trifluoromethylbenzenediazonium salt in a copper sulfate aqueous solution.

2. The process according to claim 1, wherein the amount of water in the step (1) is about 2 to 11 parts by weight based on 1 part by weight of 4-fluoro-3-trifluoromethylaniline.

3. The process according to claim 1, wherein the amount of sulfuric acid in the step (1) is about 2 to 7.5 parts by weight based on 1 part by weight of 4-fluoro-3-trifluoromethylaniline.

4. The process according to claim 1, wherein the diazotization is performed at 30° C. or lower.

5. The process according to claim 1, wherein the sulfuric acid concentration after diazotization is about 31 to 65% by weight.

6. The process according to claim 1, wherein 4-fluoro-3-trifluoromethylaniline sulfate is subjected to a diazotization reaction by using a diazotizing agent to obtain an aqueous solution of 8 to 25% by weight of a 4-fluoro-3-trifluoromethylbenzenediazonium salt, in which the content of a by-product is 0.7% by weight or less even when the aqueous solution is retained at 0° to 5° C. for 24 hours where a sulfuric acid concentration after diazotization is 30 to 70% by weight in terms of the amount of sulfuric acid added during the diazotization reaction, and the amount of water used is 1 to 20 parts by weight based on 1 part by weight of 4-fluoro-3-trifluoromethylaniline.

7. The process according to claim 1, wherein the amount of the 4-fluoro-3-trifluoromethylbenzenediazonium salt at hydrolyzing step (3) is 8 to 25% by weight.

* * * * *